US009803229B2

(12) United States Patent
Hrabak et al.

(10) Patent No.: US 9,803,229 B2
(45) Date of Patent: Oct. 31, 2017

(54) METHOD OF DETECTION OF GRAM-NEGATIVE BACTERIA PERIPLASMIC SPACE AND CELL WALL OUTER MEMBRANE PROTEINS BY MASS SPECTROMETRY

(71) Applicant: UNIVERZITA KARLOVA V PRAZE, LEKARSKA FAKULTA V PLZNI, Plzen (CZ)

(72) Inventors: Jaroslav Hrabak, Plzen (CZ); Konstantinos Papagiannitsis, Plzen (CZ)

(73) Assignee: UNIVERZITA KARLOVA V PRAZE, LEKARSKA FAKULTA V PLZNI, Plzen (CZ)

( * ) Notice: Subject to any disclaimer, the term of this patent is extended or adjusted under 35 U.S.C. 154(b) by 241 days.

(21) Appl. No.: 14/398,705

(22) PCT Filed: Jun. 20, 2014

(86) PCT No.: PCT/CZ2014/000069
§ 371 (c)(1),
(2) Date: Nov. 3, 2014

(87) PCT Pub. No.: WO2014/202034
PCT Pub. Date: Dec. 24, 2014

(65) Prior Publication Data
US 2016/0138068 A1    May 19, 2016

(30) Foreign Application Priority Data
Jun. 20, 2013    (CZ) .............................. PV 2013-473

(51) Int. Cl.
C12Q 1/18        (2006.01)
C12Q 1/34        (2006.01)
C12Q 1/04        (2006.01)
G01N 33/569      (2006.01)
G01N 33/68       (2006.01)
G01N 33/94       (2006.01)

(52) U.S. Cl.
CPC ................ C12Q 1/04 (2013.01); C12Q 1/18 (2013.01); C12Q 1/34 (2013.01); G01N 33/56911 (2013.01); G01N 33/6851 (2013.01); G01N 33/9446 (2013.01); *G01N 2333/986* (2013.01)

(58) Field of Classification Search
CPC ... C12Q 1/04; C12Q 1/18; C12Q 1/34; G01N 2333/986; G01N 33/56911; G01N 33/685; G01N 33/9446
See application file for complete search history.

(56) References Cited

U.S. PATENT DOCUMENTS

2012/0196309 A1    8/2012 Peaper et al.

FOREIGN PATENT DOCUMENTS

| DE | WO 2012113699 A1 * | 8/2012 | ............... C12Q 1/18 |
| WO | WO 2011/154517 | 12/2011 | |
| WO | WO 2012/143534 | 10/2012 | |
| WO | WO 2012/143535 | 10/2012 | |

OTHER PUBLICATIONS

Davidson, V.L. and Sun, D "Lysozyme-Osmotic Shock Methods for Localization of Periplasmic Redox Proteins in Bacteria" Methods in Enzymology, 2002, vol. 353 ,pp. 121-130.*
Nuwaysir, L.M. and Wilkins, C.L. "Matrix-assisted laser desorption by Fourier transform mass spectrometry" SPIE vol. 1437 Applied Spectroscopy in Material Science (1991), pp. 112-123.*
Drummond "Preparation of the periplasmic protein fraction of E. coli by cold osmotic shock" Drummond.openware.org, Mar. 28, 2009, 1 page.*
Sigma-Aldrich, "Lysozyme" Product Information Catalog Number, L7651, Mar. 2008, 2 pages.*
Supelco, "Trizma® Buffers: Product Specification", Sigma-Aldrich, T494109, 1996, 2 pages.*
Hrabak, J et al, "Carbapenemase Activity Detection by Matrix-Assisted Laser Desorption Ionization—Time of Flight Mass Spectrometry" Journal of Clinical Microbiology, Sep. 2011 (pub. Jul. 20, 2011), 49(9), p. 3222-3227. doi:10.1128/JCM.00984-11.*
Calderaro A, Arcangeletti MC, Rodighiero I, Buttrini M, Gorrini C, Motta F, et al. "Matrix-assisted laser desorption/ionization time-of-flight (MALDI-TOF) mass spectrometry applied to virus identification." Sci Rep, 2014 (pub. Oct. 30, 2014), 4:6803 pp. 1-7. doi: 10.1038/srep06803.*
Calderaro A, Piergianni M, Buttrini M, Montecchini S, Piccolo G, Gorrini C, et al. "MALDI-TOF mass spectrometry for the detection and differentiation of Entamoeba histolytica and Entamoeba dispar." PLoS One 2015 (pub. Apr. 15, 2015); pp. 1-16. doi:10.1371/journal.pone.0122448.*
Calderaro A, Gorrini C, Piccolo G, Montecchini S, Buttrini M, Rossi S, et al "Identification of Borrelia Species after Creation of an In-House MALDI-TOF MS Database" PLoS ONE, 2014 (pub. Feb. 12, 2014), 9(2):e88895, pp. 1-7. doi:10.1371/journal.pone.0088895.*

(Continued)

*Primary Examiner* — Chris R Tate
*Assistant Examiner* — Aaron J Kosar
(74) *Attorney, Agent, or Firm* — Notaro, Michalos & Zaccaria P.C.

(57) ABSTRACT

The invention relates to a method of detection of Gram-negative bacteria periplasmic space and cell wall outer membrane proteins by mass spectrometry, wherein the periplasmic space and cell wall outer membrane proteins are extracted from the bacteria, and the proteins to be detected are stabilized by an inhibitor and/or a substrate of the given protein, the proteins are then dissolved, placed onto a MALDI-TOF plate, covered with matrix solution, measured by MALDI-TOF mass spectrometry, and the resulting spectra are compared to the reference peaks of the given protein. Preferably, the proteins are beta-lactamases and their detection can be used to quickly determine the bacterial resistance against beta-lactam antibiotics, minimizing the false-positive results.

10 Claims, 3 Drawing Sheets

(56) References Cited

OTHER PUBLICATIONS

Marsano, Francesco "Sample preparation" Università degli Studi del Piemonte Orientale "Amedeo Avogadro" (UNIPMN), <http://people.unipmn.it/marsano/web_en/sample.html>, (retrieved online Jan. 2017), 2001, 5 pages.*

Naenna, P., et al "Detection of Outer Membrane Porin Protein, An Imipenem Influx Channel, In Pseudomonas Aeruginosa Clinical Isolates" Southeast Asian J Trop Med Public Health, May 2010, 41(3), pp. 614-624.*

* cited by examiner

METHOD OF DETECTION OF GRAM-NEGATIVE BACTERIA PERIPLASMIC SPACE AND CELL WALL OUTER MEMBRANE PROTEINS BY MASS SPECTROMETRY

FIELD OF ART

The invention relates to a method of identification of proteins of periplasmic space and of the outer membrane of a cell wall of Gram-negative bacteria using mass spectrometry. In particular it relates to a method of identification of beta-lactamases and to the detection of Gram-negative bacteria resistance towards beta-lactam antibiotics.

BACKGROUND ART

Beta-lactamases are enzymes produced by some bacteria. They are responsible for bacterial resistance towards beta-lactam antibiotics (e.g. penicillins, cephalosporins, carbapenems). A suitable method for the determination of bacterial resistance is detection of beta-lactamases. It is important for an effective antibiotic treatment and for setting of suitable precautions to block the spreading of their producers.

Beta-lactamase identification is carried out using phenotype methods based on the sensitivity towards different inhibitors. A precise identification takes place by the use of PCR amplification of the genes thereof followed by sequencing of the amplicons. There are several laboratories dealing with the development of beta-lactamase identification methods using mass spectrometry (e.g. Schaumann R, Knoop N, Genzel G H, Losensky K, Rosenkranz C, Stingu C S, Schellenberger W, Rodloff A C, Eschrich K. 2012. A step towards the discrimination of beta-lactamase-producing clinical isolates of Enterobacteriaceae and *Pseudomonas aeruginosa* by MALDI-TOF mass spectrometry. Med. Sci. Monit. 18: MT71-MT77).

The method of protein (beta-lactamase) detection using MALDI-TOF (matrix assisted laser desorption/ionization time-of-flight) mass spectrometry is capable of affording results comparable with molecular genetics assays (PCR, microchips), yet making the whole process considerably faster and cheaper. So far, no effective method of detection of these enzymes using MALDI-TOF mass spectrometry has been published. The only published work, in which beta-lactamase has been identified using MALDI-TOF mass spectrometry, is the work of Camara J E, Hays F A. 2007. Discrimination between wild-type and ampicillin-resistant *Escherichia coli* by matrix-assisted laser desorption/ionization time-of-flight mass spectrometry. Anal. Bioanal. Chem. 389: 1633-1638 from 2007. The results published by the above-mentioned authors were, however, irreproducible. At the same time there exist no publications confirming the conclusions of the above-cited work.

It is known from WO 2012/143535 and WO 2012/143534 that carbapenemases and cephalosporinases can be detected by mass spectrometry, however, the proteins are first cleaved into short peptides and the type of carbapenemases and cephalosporinases is then determined according to the spectra typical for those peptides.

Furthermore, the detection of bacterial resistance is known, wherein products of treatment with enzymes causing the resistance are followed by mass spectrometry. It involves covalently modified antibiotics or covalently modified model compounds (US 2012/196309). Likewise, there is known a determination of the presence of beta-lactamases, based on the detection of products of beta-lactamase activity, thus based on the detection of products of hydrolytic cleavage of the beta-lactam ring amide bond of beta-lactam anibiotics (WO 2011/154517).

All methods of detecting the enzymes of bacterial resistance known heretofore require either enzyme degradation into peptides or carrying out of the enzymatic reaction followed by the detection of the products of this reaction. This generates the risk of false positive results by incorporating additional components into the mixture being analyzed.

DISCLOSURE OF THE INVENTION

The present invention provides a method of detection of gram-negative bacteria periplasmic space and cell wall outer membrane proteins by mass spectrometry, wherein the periplasmic space and cell wall outer membrane proteins are extracted from the bacteria, and the proteins to be detected are stabilized by an inhibitor and/or a substrate of the respective protein to be detected. The stabilized proteins are then dissolved, deposited on a MALDI-TOF plate, covered by matrix solution and measured by a MALDI-TOF (matrix assisted laser desorption/ionization time-of-flight) mass spectrometry method. The resulting spectra are then compared with reference peaks for a given protein. Protein reference peaks are obtained from measurements of protein standards of known—or verified using known methods—identities.

The extraction is preferably carried out as follows: bacteria grown in a liquid cultivation medium appropriate for Gram-negative bacteria, e.g. Mueller-Hinton (MH) bouillon or brain-heart infusion (BHI), are cooled down to a temperature in the range of from 0° C. to 6° C., followed by a centrifugation in order to sediment the bacteria. The supernatant is discharged, the pellet is re-suspended in an aqueous solution of saccharose having the concentration of at least 20% (w/w), preferably from 20% to 40% (w/w), more preferably in a 40% (w/w) saccharose aqueous solution. The incubation is carried out for at least 1 hour at the temperature of from 2° C. to 8° C., followed by an addition of a buffer suitable for a lysozyme activity (for example Tris-HCl buffer) and the lysozyme. The mixture is then incubated at a temperature of from 35° C. to 37° C. for a time necessary to destroy the outer membrane of the cell wall and to liberate the proteins of periplasmic space (generally 1 hour minimum). The quality of the extraction/destruction of the outer membrane of a cell wall can be verified microscopically—the rod-shaped bacteria change into a spherical form (spherocytes).

In a preferred embodiment, the present invention provides a method of detection of beta-lactamases of gram-negative bacteria using mass spectrometry, wherein periplasmic space and cell wall outer membrane proteins are extracted from the bacteria, beta-lactamases in this mixture are stabilized with a beta-lactamase inhibitor and/or substrate. Beta-lactamases are further precipitated, the precipitated beta-lactamases are dissolved and deposited on a MALDI-TOF plate, covered by a matrix solution destined for ionization of proteins with Mr>10 000 and measured using MALDI-TOF mass spectrometry method. The resulting spectra are compared with reference peaks of beta-lactamases.

In a preferred embodiment, the inhibitor or substrate used for the stabilization is a beta-lactam antibiotic or a beta-lactam inhibitor, e.g. meropenem, ampicillin, clavulanic acid, cefepime, phenyl boric acid.

The precipitation is preferably performed using C1 to C4 alcohol, more preferably ethanol, or acetone, into which trifluoroacetic acid can preferably be added, more preferably 0.1 vol. % of trifluoroacetic acid.

Preferably, the precipitated stabilized beta-lactamase is dissolved in a mixture of acetonitrile and water with an addition of trifluoroacetic acid, more preferably in the mixture containing 50 vol. % of acetonitrile, 2.5 vol. % trifluoroacetic acid and water.

Beta-lactamase reference peaks can be obtained from measurements of beta-lactamase standards, whose identity is known or can be verified using known methods.

The present invention also provides a kit for the detection of beta-lactamases of Gram-negative bacteria using mass spectrometry, containing Tris-HCl buffer (pH 8.0), a lysozyme, a beta-lactamase inhibitor and/or substrate, C1 to C4 alcohol or acetone, a mixture of acetonitrile and water with an addition of trifluoroacetic acid, matrix, matrix solvent.

BRIEF OVERVIEW OF FIGURES

FIG. 1 represents examples of detection of beta-lactamases of the CMY type. The peaks corresponding to beta-lactamase are marked by an arrow. A—spectrum of the purified beta-lactamase CMY-2, B—spectrum of a sample of *Proteus mirabilis* producing beta-lactamase CMY-15, C—spectrum of a sample of *Escherichia coli* producing beta-lactamase CMY-2.

EXAMPLES

Example 1

Cultivation of Bacteria and Beta-Lactamase Extraction:

The isolate of bacteria of the family Enterobacteriaceae (the bacteria tested were *Escherichia coli, Klebsiella pneumoniae, Proteus mirabilis, Citrobacter freundii*) was inoculated into 50 mL of Mueller-Hinton bouillon (MH bouillon) or brain-heart infusion (BHI) with an addition of 50 mg/L of ampicillin; the culture was cultivated for from 12 to 18 hours at the temperature of from 35° C. to 37° C.

The media with the cultivated culture was then cooled down to the temperature of ca. 4° C. (incubation on ice for ca. 10 mM) and centrifuged for 20 mM The supernatant was discharged. The pellet was re-suspended in 90 µL of aqueous solution of saccharose (40% w/w) and incubated for 1 hour at 4° C.

In the next step, 10 µL of 1M Tris-HCl buffer (pH 8.0) was added to the mixture together with 1 µL of lysozyme (concentration 10 mg/mL); the incubation was carried out for 90 mM at the temperature of from 35° C. to 37° C. The quality of the extraction can be verified microscopically—the rod-shaped bacteria change into a spherical form (spherocytes).

The following centrifugation lasted 5 mM at 14 000 g. The supernatant containing extracted beta-lactamases was further used.

Preparation and Stabilization of Beta-Lactamases in a Mixture:

100 µL of the prepared extract was mixed with 25 µL of 100 mM meropenem (phenyl boronic acid was also tested, giving similar results) and incubated for 10 mM at room temperature. 1 mL of ice-cold ethanol with 0.1 vol. % of trifluoroacetic acid was added to the mixture, vortexed for 30 seconds and centrifuged for 20 mM at 14 000 g at the temperature of 4° C. The supernatant was then discharged, the pellet was dried at the temperature of from 35° C. to 37° C. for 10 mM, and further dissolved in 50 µL of acetonitrile solution (500 µL of acetonitrile, 475 µL of de-ionized water, 25 µL of trifluoroacetic acid). The mixture was then vortexed for 1 min.

Measurement Itself:

1 µL of the solution was placed on a MALDI plate used for MALDI-TOF mass spectrometry measurements and let to dry at room temperature. The sample was then covered by 1 µL of matrix (50% (vol.) of ethanol in water, saturated with sinapic acid) and allowed to dry. MALDI-TOF measurement followed.

Figure 1:
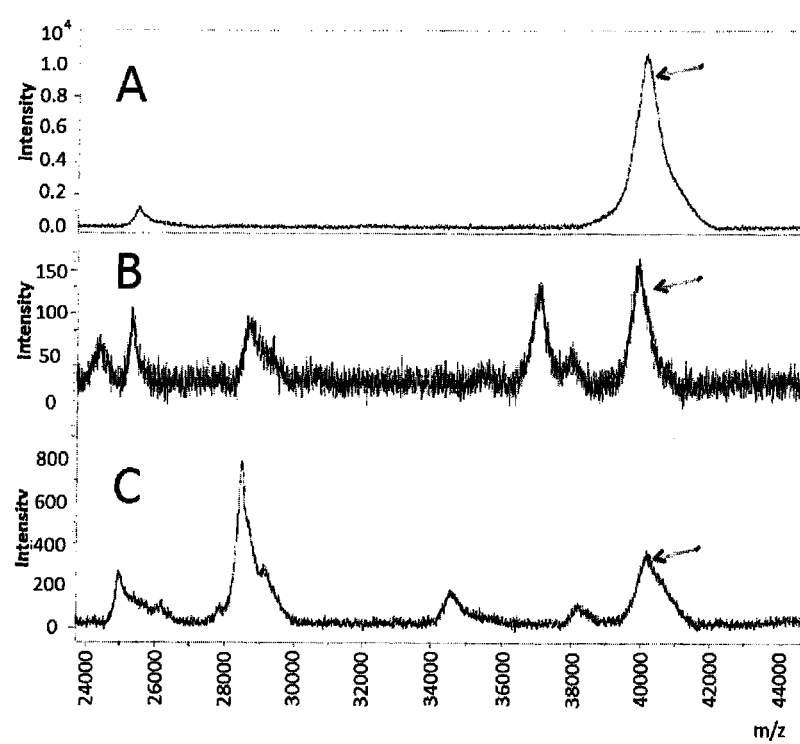
Figure 2:
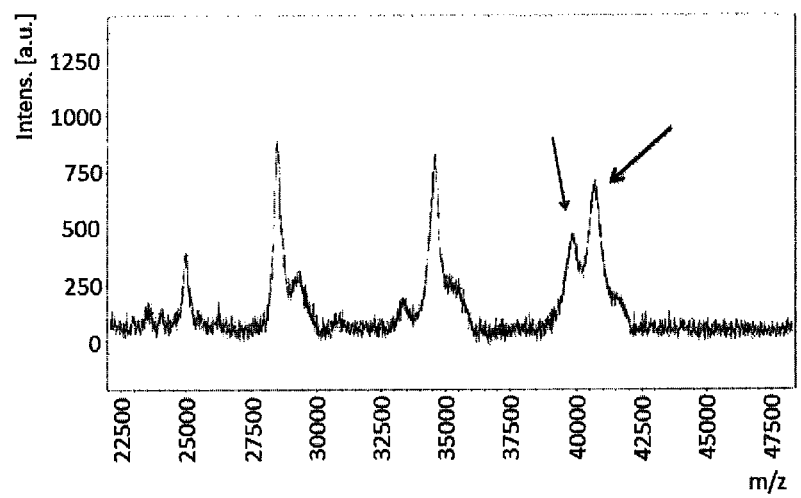
FIG. 2 represents the spectrum of *Escherichia coli*, wherein the thin arrow shows the peak of CMY-2 and the bold arrow shows the peak of the protein OmpC.
Figure 3:
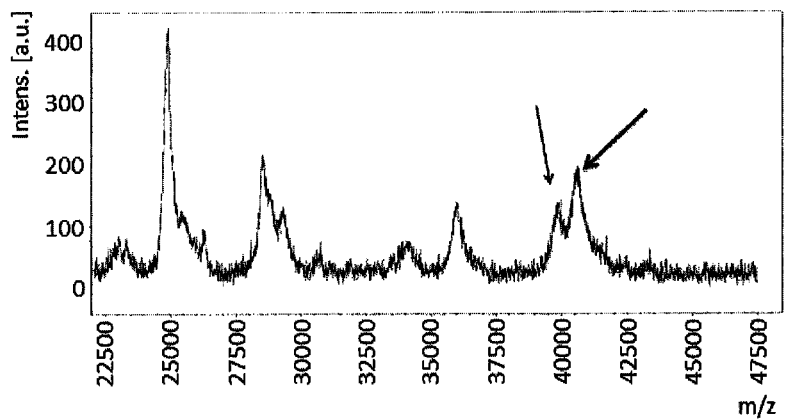
FIG. 3 represents the spectrum of *Klebsiella pneumoniae*, wherein the thin arrow shows the peak of CMY-2 and the bold arrow shows the peak of the outer membrane protein II.
Figure 4:
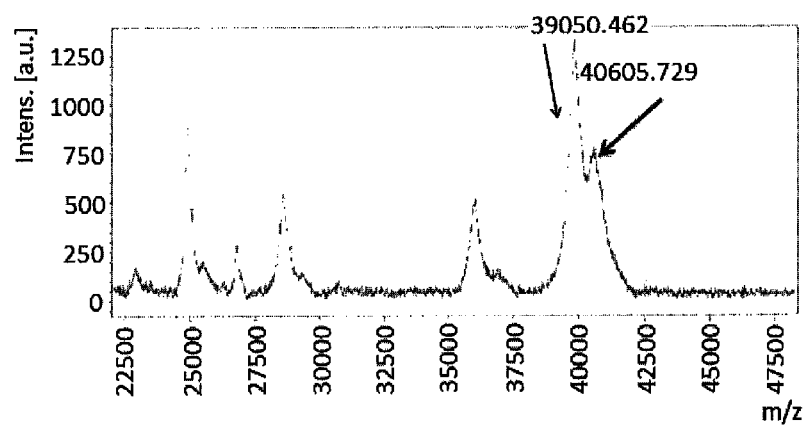
FIG. 4 represents the spectrum of *Klebsiella pneumoniae*, wherein the thin arrow shows the peak of CMY-2 and the bold arrow shows the peak of the OmpK36.
Figure 5:
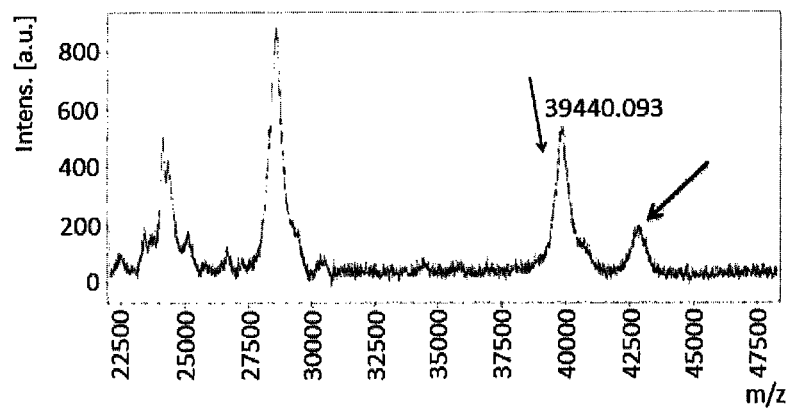
FIG. 5 represents the spectrum of *Proteus mirabilis*, wherein the thin arrow shows the peak of CMY-2 and the bold arrow shows the peak of the flagellin.

FIG. 1 shows spectra with separated peaks which are easy to integrate and which have a very good signal-to-noise ratio, obtained by using the method according to the present invention.

FIGS. 2 to 5 show spectra with separated peaks of beta-lactamases and other periplasmic space and cell wall outer membrane proteins, obtained by the procedure described in example 1, using meropenem for stabilization of the proteins.

The invention claimed is:

1. A method of detection of gram-negative bacteria periplasmic space β-lactamases by MALDI-TOF mass spectrometry, the method comprising:
    (a) obtaining β-lactamases from gram-negative bacteria;
    (b) contacting the β-lactamases with an effective amount of an inhibitor of and/or a substrate of the β-lactamases so as to stabilize the β-lactamases;
    (c) dissolving the stabilized β-lactamases;
    (d) placing suitable amounts of the dissolved β-lactamases onto a MALDI-TOF plate and coating the placed β-lactamases with a matrix solution;
    (e) measuring the spectra of the β-lactamases from step (d) by MALDI-TOF mass spectrometry; and
    (f) comparing the measured spectra from step (e) and/or peaks thereof to one or more reference β-lactamases spectra and/or peaks thereof, thereby detecting the periplasmic space β-lactamase.

2. The method according to claim 1, wherein step (a) comprises:
    (i) cooling down a culture medium containing the gram-negative bacteria to a temperature of from 0° C. to 6° C.;
    (ii) centrifuging the cooled culture medium so as to sediment the bacteria into a pellet;
    (iii) re-suspending the pellet in an aqueous solution containing at least 20% (w/v) saccharose;
    (iv) incubating the suspension from (iii) for at least 1 hour at the temperature of from 2° C. to 8° C., thereby providing an incubated mixture;
    (v) adding a buffer solution containing lysozyme to the incubated mixture; and (vi) incubating the resulting lysozyme-added mixture from step (v) at the temperature of from 35° C. to 37° C.

3. A method of detecting gram-negative bacteria periplasmic space β-lactamases by MALDI-TOF mass spectrometry, the method comprising:
(a) obtaining β-lactamases from gram-negative bacteria;
(b) contacting the β-lactamases with an effective amount of an inhibitor of and/or a substrate of the β-lactamases so as to stabilize the β-lactamases;
(c) dissolving the stabilized β-lactamases,
(d) precipitating the dissolved β-lactamases,
(e) dissolving the precipitated β-lactamases,
(f) placing suitable amounts of the dissolved β-lactamases from step (e) onto a MALDI-TOF plate and coating the placed β-lactamases with a matrix solution, wherein the matrix solution is a solution suitable for ionization of proteins with molecular mass greater than 10,000 Da,
(g) measuring the spectra of the β-lactamases from step (f) by MALDI-TOF mass spectrometry; and
(h) comparing the measured spectra from step (g) and/or peaks thereof to one or more reference β-lactamase spectra and/or peaks thereof, thereby detecting the periplasmic space β-lactamases.

4. The method according to claim 3, wherein step (a) comprises:
(i) cooling down a culture medium containing the gram-negative bacteria to a temperature of from 0° C. to 6° C.;
(ii) centrifuging the cooled culture medium so as to sediment the bacteria into a pellet;
(iii) re-suspending the pellet in an aqueous solution containing at least 20% (w/v) saccharose;
(iv) incubating the suspension from (iii) for at least 1 hour at the temperature of from 2° C. to 8° C., thereby providing an incubated mixture;
(v) adding a buffer solution containing lysozyme to the incubated mixture; and then
(vi) incubating the resulting lysozyme-added mixture from step (v) at the temperature of from 35° C. to 37° C. for at least one hour.

5. The method according to claim 3, wherein the inhibitor or substrate is a β-lactam antibiotic or a β-lactam inhibitor, and the inhibitor or substrate is selected from the group consisting of meropenem, ampicillin, clavulanic acid, cefepim, and phenyl boric acid.

6. The method according to claim 3, wherein the precipitation is performed by contacting the stabilized β-lactamase with a solution of C1 to C4 alcohol or acetone.

7. The method according to claim 3, wherein the dissolving of the precipitated stabilized β-lactamase is carried out by contacting the precipitated stabilized β-lactamase with a mixture of acetonitrile and water and an amount of trifluoroacetic acid.

8. The method according to claim 3, wherein the precipitating is performed by contacting the stabilized β-lactamase with a solution of C1 to C4 alcohol or acetone, and an amount of trifluoroacetic acid.

9. The method according to claim 3, wherein the precipitating is performed by contacting the stabilized β-lactamase with a solution of C1 to C4 alcohol or acetone, and 0.1 vol. % of trifluoroacetic acid.

10. The method according to claim 3, wherein the dissolving of the precipitated stabilized β-lactamase is carried out using a mixture of acetonitrile, water and 2.5 vol. % of trifluoroacetic acid.

\* \* \* \* \*